United States Patent
Xu et al.

(10) Patent No.: US 11,192,921 B2
(45) Date of Patent: Dec. 7, 2021

(54) POLYPEPTIDE HAVING ANALGESIC ACTIVITY AND USE THEREOF

(71) Applicant: NANJING ANJI BIOLOGICAL TECHNOLOGY CO., LTD, Nanjing (CN)

(72) Inventors: Hanmei Xu, Nanjing (CN); Chen Liu, Nanjing (CN)

(73) Assignee: NANJING ANJI BIOLOGICAL TECHNOLOGY CO., LTD, Nanjing (CN)

( * ) Notice: Subject to any disclaimer, the term of this patent is extended or adjusted under 35 U.S.C. 154(b) by 0 days.

(21) Appl. No.: 16/762,948

(22) PCT Filed: May 2, 2018

(86) PCT No.: PCT/CN2018/085275
§ 371 (c)(1),
(2) Date: May 11, 2020

(87) PCT Pub. No.: WO2019/095639
PCT Pub. Date: May 23, 2019

(65) Prior Publication Data
US 2020/0361990 A1    Nov. 19, 2020

(30) Foreign Application Priority Data
Nov. 14, 2017 (CN) .......................... 201711122000.9

(51) Int. Cl.
*C07K 7/08* (2006.01)
*A61P 29/00* (2006.01)

(52) U.S. Cl.
CPC ................ *C07K 7/08* (2013.01); *A61P 29/00* (2018.01)

(58) Field of Classification Search
CPC .................................. C07K 7/08; A61P 29/00
See application file for complete search history.

*Primary Examiner* — Amber D Steele
(74) *Attorney, Agent, or Firm* — Wen IP LLC; Zhihua Han

(57) ABSTRACT

A polypeptide with analgesic activity and use thereof is disclosed. The polypeptide has the amino acid sequence of $X_a$-$X_b$-Cys-Ser-Thr-Pro-Pro-$X_c$-$X_d$-Val-Leu-Tyr-$X_e$ (SEQ ID NO: 1), or a pharmaceutically acceptable salt thereof, wherein the $X_a$ is Gly or deleted, the $X_b$ is one of Ser or Lys; the $X_c$ is one of d-Cys or Ser or Asp, the $X_d$ is Ala or deleted; and the $X_e$ is Cys or Ser. One pair of disulfide bonds are formed between two cysteines in the sequence. The polypeptide has good inhibitory effects on physicochemical irritating pain and pathological and neuropathic pain, and has good analgesic effects in various experimental models. The specific effects of the polypeptide are to significantly increase the threshold of pain of mice, prolong the heat tolerance time of mice, and the adverse reactions such as spontaneous movement and excitability of mice are lower than normal values.

5 Claims, No Drawings
Specification includes a Sequence Listing.

POLYPEPTIDE HAVING ANALGESIC ACTIVITY AND USE THEREOF

TECHNICAL FIELD

The present invention belongs to the field of biological drugs, and more specifically relates to a polypeptide with analgesic activity and use thereof.

BACKGROUND

The process of pain generation is relatively complex, involving pain receptors, conduction nerves, pain centers and other factors. The main causes of pain are as follows: (1) a series of external mechanical stimuli and local edema of tissues during inflammatory reactions can compress nerve endings and cause pain; (2) physical and chemical stimuli excite the pain center through sensory neurons, causing pain; (3) pathological injury of peripheral nerves stimulates sympathetic nerve fibers and finally stimulates excessive excitement in the cerebral cortex, causing neuropathic pain; (4) algogenic substances released by injured cells or nociceptors after the body is stimulated by the outside world will stimulate local receptors to excite the central nervous system to cause pain.

Early analgesics may be roughly divided into non-steroidal drugs (aspirin), opioid receptors (conotoxin) and other auxiliary analgesics (anticonvulsants). They have good effects on chronic pain, neuropathic pain and inflammations, but their limitations and side effects have always been a bottleneck problem and cannot be well solved. For example, aspirin is more harmful to the human circulatory system, especially the digestive and hematopoietic system; the conotoxin has a series of adverse reactions such as serious addiction, tolerance and respiratory distress; and the allergies and side effects of the anticonvulsants have not been well improved. Finding analgesics with novel targets or creating and optimizing compounds with novel structures have always been an issue that pharmaceutical researchers need to resolve urgently. Compared with conventional analgesics, analgesic polypeptides acting on ion channels bring new dawn to researchers due to their wide sources, little toxic side effects, long half life, obvious efficacy and other characteristics. Ion channels of biomembrane are membrane proteins that penetrate through lipid bilayers of cell membranes and have hydrophilic pores in the center, which are the basis for the generation of bioelectricity in nerves, skeletal muscles, and myocardial cells, etc. Such channels are closely related to various life activities such as receptor potential generation, nerve excitation and conduction, and central nervous system regulation, and are accompanied by high selectivity. Based on the specific ion channel of biomembrane only allows one or several specific ions to be hypertonic, the ion channels of biomembrane may be divided into sodium ion channels, potassium ion channels, calcium ion channels, and acid-sensitive ion channels, etc. In general, $Ca^{2+}$ and $K^+$ ions keep balance between the inside and outside of the cell membrane. By adjusting the concentrations of potassium ions and sodium ions in the central nervous system, the excitability of neurons can be inhibited, which is also a mechanism for the central nervous system to exert central analgesic effects. The activity of $Na^+$ ion channels determines the formation and transmission of pain impulses. Many analgesics block the conduction path of pain excitation by inhibiting voltage-gated sodium ion channels. In recent years, with the in-depth study on the molecular mechanism of pain, researchers have found that the conformational changes of ion channels are closely related to whether the body produces pain, and sodium ion channel ($Na_v$) plays the most important role. Modern molecular biology studies show that subtype $Na_v1.7$ is a novel target for pain treatment. When exerting normal physiological functions, the subtype $Na_v1.7$ can depolarize excited cells and transmit signal molecules from the posterior horn of gray matter to nociceptors through synapses, finally making the body feel pain. There are a large number of polypeptides acting on ion channels in animal toxins, which have a great development space. At present, several well-studied polypeptide structures include μ-SLPTXSsm6a extracted from Scolopendra subspinipes mutilans, BmK-AGAP extracted from Buthus martensii Karsch, HWTX-I extracted from Ornithoctonus huwena, and Mambalgins extracted from Dendroaspis polylepis, etc.

The research on conotoxin polypeptides has always been a hot topic in the field. For example, Chinese patent No. 201480082283.7, which was published on May 31, 2017, discloses a conotoxin polypeptide κ-CPTx-bt105, and a preparation method and use thereof. The conotoxin polypeptide consists of 16 amino acids, and has the molecular weight of 1626.62 Daltons and the complete sequence of GICCVDDTCTTHSGCL (SEQ ID NO: 5). The conotoxin polypeptide has the effects of inhibiting a potassium ion channel current and relieving pain. However, at present, the method of extracting the conotoxin polypeptide from conus is relatively complex, and the conotoxin polypeptide has certain side effects, which cause serious physical and psychological dependence.

SUMMARY

Problems to be Solved

In view of the side effects of existing conotoxin polypeptide, the present invention provides a polypeptide with analgesic activity and use thereof. The polypeptide has a significant improvement in structural stability and analgesic activity compared with conotoxin, and it is weaker than conotoxin in adverse reactions such as body injury.

Technical Solution

In order to solve the foregoing problems, the technical solutions adopted by the present invention are as follows:

A polypeptide with analgesic activity or a pharmaceutically acceptable salt thereof is provided, wherein the polypeptide has the amino acid sequence of $X_a$-$X_b$-Cys-Ser-Thr-Pro-Pro-$X_c$-$X_d$-Val-Leu-Tyr-$X_e$ (SEQ ID NO: 1).

Further, the $X_a$ is Gly or deleted, the $X_b$ is one of Ser or Lys; the $X_c$ is one of d-Cys or Ser or Asp, the $X_d$ is Ala or deleted; and the $X_e$ is Cys or Ser.

Further, the amino acid sequences of the polypeptides are:

```
polypeptide I:
                                        (SEQ ID NO: 2)
Gly-Ser-Cys-Ser-Thr-Pro-Pro-d{Cys}-Val-Leu-Tyr- Ser;

polypeptide II:
                                        (SEQ ID NO: 3)
Gly-Ser-Cys-Ser-Thr-Pro-Pro-Ser-Ala-Val-Leu-Tyr- Cys;
or
```

```
polypeptide III:
                                           (SEQ ID NO: 4)
Lys-Cys-Ser-Thr-Pro-Pro-Asp-Ala-Val-Leu-Tyr-Cys.
```

Further, one pair of disulfide bonds are formed between two cysteines in each of the polypeptide sequence.

Further, a polypeptide with analgesic activity or a pharmaceutically acceptable salt thereof is provided, wherein the polypeptide has the sequence obtained by deleting, replacing or adding one or more amino acids on the basis of the above sequence.

The use of the above polypeptide in preparing a product for preventing and/or treating pain is provided.

Provided is a product for preventing and/or treating pain, wherein its active ingredient is the above polypeptide.

The above product may specifically be a drug.

When needed, one or more pharmaceutically acceptable auxiliary materials can also be added to the above drug. The auxiliary materials include diluents, excipients, fillers, adhesives, wetting agents, absorption enhancers, surfactants, lubricants, stabilizers and the like that are conventional in the pharmaceutical field.

The drug of the present invention can be made into various forms such as injections, dry powder injections, tablets or granules. The drugs in various dosage forms can be prepared according to conventional methods in the pharmaceutical field.

Further, the pain includes physicochemical irritating pain and pathological or neuropathic pain.

At present, there are mainly anti-inflammatory analgesics and opioid analgesics in clinical application. The anti-inflammatory analgesics are clinically mainly used for treating chronic dull pain such as headache, toothache, muscle and joint pain and dysmenorrhea. These drugs are not addictive and are widely used clinically. The opioid analgesics (narcotic analgesics) are a class of drugs that can eliminate or relieve pain and change the emotional response to pain. However, they have certain side effects, such as constipation, lethargy, insensitivity, nausea, vomiting, respiratory depression and dependence, which cause serious physical and psychological dependence. Consequently, their clinical application is severely limited. In addition to the narcotic analgesics, many drugs acting on the central nervous system, such as antidepressants, anticonvulsants and neuroleptics, are used to control pain. These drugs have direct analgesic effects or potential analgesic activity to a certain extent, but their side effects become more severe with the increase of dosage. For example, aspirin has great damage to the human circulatory system, especially the digestive and hematopoietic system; the conotoxin has a series of adverse reactions such as serious addiction, tolerance and respiratory distress; and the allergies and side effects of the anticonvulsants have not been well improved. In view of this, the present invention provides a self-designed polypeptide structure having stronger analgesic activity and lower toxic side effects, on the basis of analysis of a large number of conventional structures and pharmacological experiments through the computer three-dimensional simulation technology. According to the analysis of the structures of various existing analgesic polypeptides, the present invention has independently designed an analgesic polypeptide with a novel structure acting on ion channels by utilizing the three-dimensional structure. Various experimental models prove that the polypeptide has the same analgesic effect as conotoxin and low adverse reactions such as tolerance, thus having great development prospects.

Beneficial Effects

Compared with the prior art, the present invention has the following beneficial effects:

(1) The polypeptide of the present invention has a simple structure, is easy to synthesize, separate and purify, and effectively retains and improves the analgesic activity of conotoxin.

(2) The adverse reactions and toxic side reactions of the polypeptide of the present invention are weak.

(3) The polypeptide of the present invention has good analgesic effects in various experimental models. The specific effects of the polypeptide are to significantly increase the threshold of pain of mice, prolong the heat tolerance time of mice, and the adverse reactions such as spontaneous movement and excitability of mice are lower than normal values.

DETAILED DESCRIPTION

The present invention is further described below with reference to specific examples. The following descriptions are only preferred embodiments of the present invention and are not intended to limit the present invention in any other form. Any person skilled in the art may use the technical content disclosed above to change to equivalent embodiments with equivalent changes. Without departing from the content of the solution of the present invention, any simple modifications or equivalent changes made to the following examples according to the technical essence of the present invention fall within the protection scope of the present invention.

Example 1

The present invention relates to a polypeptide with analgesic activity or a pharmaceutically acceptable salt thereof, wherein the parent nucleus structure of the polypeptide has an amino acid sequence $X_a$-$X_b$-Cys-Ser-Thr-Pro-Pro-$X_c$-$X_d$-Val-Leu-Tyr-$X_e$ (SEQ ID NO: 1), and wherein the $X_a$ may be Gly or deleted, the $X_b$ may be one of Ser or Lys; the $X_c$ may be one of d-Cys or Ser or Asp, and the $X_d$ may be Ala or deleted; and the $X_e$ may be Cys or Ser. Specifically, the amino acid sequences of the polypeptides are:

```
polypeptide I:
                                        (SEQ ID NO: 2)
Gly-Ser-Cys-Ser-Thr-Pro-Pro-d{Cys}-Val-Leu-Tyr- Ser;

polypeptide II:
                                        (SEQ ID NO: 3)
Gly-Ser-Cys-Ser-Thr-Pro-Pro-Ser-Ala-Val-Leu-Tyr- Cys;
or polypeptide III:
                                        (SEQ ID NO: 4)
Lys-Cys-Ser-Thr-Pro-Pro-Asp-Ala-Val-Leu-Tyr-Cys.
```

Or, provided is a polypeptide that has a sequence obtained by deleting, replacing or adding one or more amino acids on the basis of the above sequence. One pair of disulfide bonds are formed between two cysteines in the sequence. The polypeptide has good inhibitory effects on physicochemical irritating pain and pathological and neuropathic pain.

In this example, the polypeptide I, polypeptide II and polypeptide III were mainly taken as objects to study their pain inhibiting activity. The polypeptide was synthesized by Nanjing GenScript Biotech Corporation with a purity of more than 95%.

Inhibitory effect of the analgesic polypeptides on pain in analgesic experiments with hot plate method Female Kunming mice, each weighing 20±2 g were used. The indoor temperature was kept at 22-25° C. The mice were placed on a thermostatic metal plate at 55° C. and kept at the constant temperature (within +/−0.5° C.). The time when the mice contacted the metal plate to the time when the mice licked hind feet or had hopping reaction was taken as the pain threshold index.

1. Experimental Animals: Female Kunming Mice

The mice were raised in experimental rat cages with ventilation systems. The feeding temperature was about 23° C. Normal day and night turnover alternation was performed. All experimental animals had free access to water and food. The purchased experimental animals were fed in this laboratory for 3-5 days to adapt to the experimental environment, and all animal experiments were conducted from 8:00 to 18:00. The experimental animals were kept in single cages after surgery.

2. Experimental equipment: an electronic balance, a hot plate tester, cage ventilation systems, a 1 mL syringe, and an ultra-pure water system 3. Experimental reagents: conotoxin, 0.9% of NaCl solution, polypeptide I, polypeptide II and polypeptide III.

The structure of the conotoxin polypeptide (BuIA typing) used in the present invention is Gly-Cys-Cys-Ser-Thr-Pro-Pro-Cys-Ala-Val-Leu-Tyr-Cys (SEQ ID NO 6), wherein C1-C3 and C2-C4 are cyclic.

4. Experimental method: Before the experiment, the basic pain threshold was measured twice at an interval of 5 min and then the average value was calculated. Mice with latency less than 5 s or more than 30 s were excluded. In order to prevent burns on the feet of mice, 60 s was set as the cut-off time. The qualified mice were divided into negative control group, positive control group and conotoxin group according to the random number table, with 10 mice in each group.

There were 5 groups in total: normal saline group, conotoxin group, polypeptide I group, polypeptide II group and polypeptide III group, with 10 mice in each group. The normal saline group using 0.9% NaCl solution was taken as the negative control group; the conotoxin group with a conotoxin dose of 1 μg/kg was taken as the positive control group; and the polypeptide groups with the dosage of 2 nmol/kg were taken as the experimental groups. The route of administration: intraperitoneal injection.

The pain threshold of mice was respectively recorded again 15, 30, 45, 60, 75 and 90 min after administration. The experiment was repeated three times independently. The results were expressed by x̄±S, and the statistical T test was performed. The polypeptide groups were compared with the normal saline negative control group; when *P<0.05, it indicated significant difference; and when **P<0.01, it indicated extremely significant difference. The polypeptide groups were compared with the conotoxin positive control group; when ^P<0.05, it indicated significant difference, and when ^^P<0.01, it indicated extremely significant difference. The duration of tolerance of mice to the hot plate before and after administration was compared in each group, and the pain thresholds of mice were compared between the groups. The possible maximum analgesic percentage after administration was calculated and the analgesic effects of the drugs were evaluated.

$$PMAP = \frac{\text{Pain threshold after administration} - \text{Basic pain threshold before administration}}{60 - \text{Basic pain threshold before administration}} \times 100\%$$

TABLE 1

Test results of pain thresholds of mice in various time periods in analgesic experiments with hot plate method

| Group | \multicolumn{7}{c}{Pain threshold/s} |
|---|---|---|---|---|---|---|---|
| | 0 min | 15 min | 30 min | 45 min | 60 min | 75 min | 90 min |
| Normal saline | 25.49 ± 0.38 | 23.23 ±0.14 | 25.14 ± 0.47 | 21.21 ± 0.24 | 22.24 ± 0.51 | 23.41 ± 0.23 | 24.23 ± 0.24 |
| Conotoxin | 27.29 ± 0.48 | 29.32 ± 0.18 | 24.1 ± 0.28 | 30.39 ± 0.28 | 27.39 ± 0.28 | 26.21 ± 0.38 | 24.63 ± 0.12 |
| Polypeptide I | 28.32 ± 0.21* | 25.21 ± 0.42^^ | 31.32 ± 0.32*^ | 24.23 ± 0.42^ | 21.39 ± 0.45^ | 29.23 ± 0.42* | 23.44 ± 0.24* |
| Polypeptide II | 27.43 ± 0.54^ | 42.54 ± 0.24^ | 22.33 ± 0.36* | 27.45 ± 0.52* | 31.34 ± 0.45*^ | 25.43 ± 0.54^ | 26.24 ± 0.42* |
| Polypeptide III | 29.22 ± 0.11* | 31.22 ± 0.42^^ | 33.12 ± 0.32*^ | 27.23 ± 0.42^ | 21.49 ± 0.45^ | 32.14 ± 0.42* | 21.43 ± 0.24* |

Note:
Compared with the normal saline group, *P < 0.05, **P < 0.01.
Compared with the conotoxin positive control group, ^P < 0.05, ^^P < 0.01.

5. Experimental Results:

5.1 Test Results of Heat Thresholds of Mice

The polypeptide groups can play an analgesic role in animal models for analgesic experiments with a hot plate. The results are shown in Table 1: compared with the normal saline negative control group, the polypeptide I group, the polypeptide II group and the polypeptide III group could effectively increase the heat thresholds of mice. The increase of the pain threshold of the polypeptide II group was significantly higher than that of the normal saline group and that of the conotoxin group. The experimental results have statistical significance.

5.2 PMAP Evaluation Results

PAMP was calculated to be about 47.57%. Compared with the conotoxin group, the polypeptide groups have no significant difference in analgesic effect and have a good analgesic effect.

Example 2

Inhibitory Effect of the Analgesic Polypeptides on Pain in Heat Radiation Tail Flick Experiments Kunming mice (half male and half female), each weighing 20±2 g were used. The indoor temperature was kept at 22-25° C. A small spotlight was used to generate the light beam with certain intensity, and the tail of each mouse was focused and irradiated through a lens to cause pain. During the experiment, the tail of the mouse was placed on a tail groove of a tail flick pain threshold detector, and a light spot fell on the middle-lower ⅓ of the tail of the mouse (before the experiment, the point was marked with a pen, so that the pain threshold measuring point was at the same position each time). A tail flick latency (TFL) from the beginning of radiant heat irradiation to the occurrence of tail flick reaction was the pain reaction index.

Before administration, the basic pain thresholds of all mice were first determined, and mice with reaction latency less than 1 s or more than 3 s were excluded. In order to prevent burns on the tail of mice, 10 s was set as the cut-off time. The mice with the basic pain thresholds meeting the standard were divided into negative control group, positive control group, conotoxin group according to the random number table, with 10 mice in each group.

There was normal saline group, conotoxin group, polypeptide I group, polypeptide II group and polypeptide III group, with 10 mice in each group. The normal saline group was taken as the negative control group; the conotoxin group with a conotoxin dose of 1 μg/kg was taken as the positive control group; and each polypeptide group had the dosage of 2 nmol/kg. The route of administration: lateral ventricle administration.

The pain thresholds at the time of 5 min, 15 min, 30 min, 45 min, 60 min, 90 min and 120 min after administration were recorded respectively, and the results were expressed by $\bar{x} \pm S$. The duration of tolerance of mice to the heat radiation before and after administration was compared in each group, and the pain thresholds of mice were compared between the groups. The pain threshold increase percentage after administration was calculated and the analgesic effects of the drugs were evaluated.

$$PMAP = \frac{\text{Pain threshold after administration } - \text{Basic pain threshold before administration}}{60 - \text{Basic pain threshold before administration}} \times 100\%$$

significantly different from the conotoxin group during a time period ($^{\wedge\wedge}P<0.01$). At the dose of 2 nmol/kg, the polypeptide III group was significantly different from the normal saline group during a time period (**$P<0.01$). The experimental results have statistical significance.

2. PMAP Evaluation Results

PAMP was calculated to be about 38.32%. Compared with the conotoxin group, the polypeptide groups have no significant difference in analgesic effect and have a good analgesic effect.

Example 3

Influence of Analgesic Polypeptides on Spontaneous Activity and Exploratory Behavior of Mice in Open Field Tests 1. Materials and Method 1.1 Experimental Animals Sixty female Kunming mice were used.

Feeding conditions: room temperature (23±1)° C.; humidity (50±5)%; lighting by fluorescent lamps, with a light-dark period of 12/12 (lighting time 7:00-19:00); and animals had free access to water and food.

1.2 Experimental Instruments

A computer real-time monitoring and analysis system SMART VIDEO-TRACKING (US, SMARTv3.0.02) was used. The instrument is mainly composed of four 40 cm×40 cm×40 cm experimental open boxes, and the center of the top of each box is provided with a camera connected with a recording system. Real-time images of mice were analyzed by the system to obtain behavioral data of the mice in the open field.

2. Experimental Method:

Before the beginning of the experiment, the weight of each mouse was statistically tested, and the unqualified mice were excluded. Then the mice were divided into negative control group, positive control group, polypeptide I group, polypeptide II group and polypeptide III group according to the random number table. The normal saline group as the negative control group was injected with 0.9% NaCl solution; the conotoxin group with a conotoxin dose of 1 μg/kg was taken as the positive control group; and each polypep-

TABLE 2

Influence of CTX modified peptide on analgesic effect of tail flick in mice (n =10) (i.p)

| Group | Pain threshold/s | | | | | | |
|---|---|---|---|---|---|---|---|
| | 0 min | 15 min | 30 min | 45 min | 60 min | 75 min | 90 min |
| Normal saline | 2.60 ± 0.35 | 2.24 ± 0.57 | 2.27 ± 0.369 | 2.32 ± 0.24 | 2.42 ± 0.23 | 2.23 ± 0.13 | 2.12 ± 0.24 |
| Conotoxin | 2.23 ± 0.18 | 2.32 ± 0.28 | 2.21 ± 0.12 | 2.31 ± 0.18 | 2.12 ± 0.12 | 2.12 ± 0.12 | 2.63 ± 0.12 |
| Polypeptide I | 2.31 ± 0.12* | 2.12 ± 0.21$^{\wedge\wedge}$ | 2.12 ± 0.12* | 3.22 ± 0.12$^{\wedge}$ | 2.12 ± 0.21*$^{\wedge}$ | 2.12 ± 0.12** | 2.32 ± 0.14* |
| Polypeptide II | 2.43 ± 0.21$^{\wedge}$ | 2.52 ± 0.24** | 2.31 ± 0.36* | 2.45 ± 0.12* | 2.12 ± 0.41* | 2.23 ± 0.14$^{\wedge}$ | 2.24 ± 0.12* |
| Polypeptide III | 2.31 ± 0.22* | 2.22 ± 0.21$^{\wedge\wedge}$ | 2.32 ± 0.12* | 4.12 ± 0.12$^{\wedge}$ | 2.12 ± 0.21* | 2.14 ± 0.12** | 3.12 ± 0.14* |

Note:
Compared with the normal saline group, *$P < 0.05$, **$P < 0.01$.
Compared with the conotoxin positive control group, $^{\wedge}P < 0.05$, $^{\wedge\wedge}P < 0.01$.

Experimental Results:

1. Test Results of Heat Thresholds of Mice

The polypeptide groups can play an analgesic role in animal models for heat radiation tail flick experiments on mice. The results are shown in Table 2: compared with the normal saline negative control group, the polypeptide groups could effectively increase the heat thresholds of mice. At the dose of 2 nmol/kg, the polypeptide I group was tide group had the dosage of 2 nmol/kg. The route of administration was intraperitoneal injection.

First, it was confirmed that the open field device was clean and odorless. The numbers, dates and statuses of mice were recorded in operating software; then animals for experiments must be sent to special temporary cages of the behavioral laboratory in advance to adapt to the environment for about 3 hours to reduce animal tension; the mice were taken out of the cages (the mice faced away from the experimenter) and placed in the center of the device and then an upper cover of the device was closed quickly and gently. The video recording system was opened to record the activities of the mice in the open field. The operations were performed for 5 min. After observation, the inner walls and bottom surfaces of the square boxes were cleaned in time with 75% ethanol so as to prevent the results of the next test from being affected by the remaining information of the last animal (such as animal's excrement, urine and smell). Finally, this batch of mice were put back into the cage and the next batch of mice were tested. According to the foregoing steps, relevant indexes of all mice were detected again 1 h and 24 h after the observation, respectively. Origin 8.0 software was used to calculate the residence time in the center area, movement duration, wall climbing times and number of crossing grids of the mice as final data.

3. Experimental Results:

TABLE 3

Movement distances (m) of mice in open field tests

| Time | Normal saline | Conotoxin | Polypeptide I | Polypeptide II | Polypeptide III |
|---|---|---|---|---|---|
| 0 | 20.84 ± 1.29 | 21.03 ± 1.73 | 20.57 ± 1.65 | 20.98 ± 1.28 | 21.28 ± 1.28 |
| 1 h | 19.89 ± 1.33 | 16.92 ± 1.43* | 20.39 ± 1.21^ | 19.47 ± 1.32^ | 18.27 ± 1.22^ |
| 24 h | 18.48 ± 2.39 | 18.74 ± 1.98 | 18.99 ± 1.48 | 19.03 ± 2.48 | 19.13 ± 2.38 |

Note:
Compared with the normal saline group, *$P < 0.05$, **$P < 0.01$.
Compared with the conotoxin positive control group, ^$P < 0.05$, ^^$P < 0.01$.

TABLE 4

Number of entrances to the center area in open field tests on mice

| Time | Normal saline | Conotoxin | Polypeptide I | Polypeptide II | Polypeptide III |
|---|---|---|---|---|---|
| 0 | 20.84 ± 1.29 | 21.03 ± 1.73 | 20.57 ± 1.65 | 20.98 ± 1.28 | 21.28 ± 1.28 |
| 1 h | 19.89 ± 1.33 | 16.92 ± 1.43* | 20.39 ± 1.21^ | 19.47 ± 1.32^ | 18.47 ± 0.32^ |
| 24 h | 18.48 ± 2.39 | 18.74 ± 1.98 | 18.99 ± 1.48 | 19.03 ± 2.48 | 18.23 ± 1.48 |

Note:
Compared with the normal saline group, *$P < 0.05$, **$P < 0.01$.
Compared with the conotoxin positive control group, ^$P < 0.05$, ^^$P < 0.01$.

TABLE 5

Number of entrances to the peripheral area in open field tests on mice

| Time | Normal saline | Conotoxin | Polypeptide I | Polypeptide II | Polypeptide III |
|---|---|---|---|---|---|
| 0 | 20.84 ± 1.29 | 21.03 ± 1.73 | 20.57 ± 1.65 | 20.98 ± 1.28 | 21.28 ± 1.38 |
| 1 h | 19.89 ± 1.33 | 16.92 ± 1.43* | 20.39 ± 1.21^ | 19.47 ± 1.32^ | 18.57 ± 1.42^ |
| 24 h | 18.48 ± 2.39 | 18.74 ± 1.98 | 18.99 ± 1.48 | 19.03 ± 2.48 | 17.13 ± 2.18 |

Note:
Compared with the normal saline group, *$P < 0.05$, **$P < 0.01$.
Compared with the conotoxin positive control group, ^$P < 0.05$, ^^$P < 0.01$.

TABLE 6

Residence time (s) in the center area in open field tests on mice

| Time | Normal saline | Conotoxin | Polypeptide I | Polypeptide II | Polypeptide III |
|---|---|---|---|---|---|
| 0 | 20.84 ± 1.29 | 21.03 ± 1.73 | 20.57 ± 1.65 | 20.98 ± 1.28 | 21.78 ± 1.17 |
| 1 h | 19.89 ± 1.33 | 16.92 ± 1.43* | 20.39 ± 1.21^ | 19.47 ± 1.32^ | 18.37 ± 1.22^ |
| 24 h | 18.48 ± 2.39 | 18.74 ± 1.98 | 18.99 ± 1.48 | 19.03 ± 2.48 | 18.13 ± 1.38 |

Note:
Compared with the normal saline group, *$P < 0.05$, **$P < 0.01$.
Compared with the conotoxin positive control group, ^$P < 0.05$, ^^$P < 0.01$.

TABLE 7

Residence time (s) in the peripheral area in open field tests on mice

| Time | Normal saline | Conotoxin | Polypeptide I | Polypeptide II | Polypeptide III |
|---|---|---|---|---|---|
| 0 | 20.84 ± 1.29 | 21.03 ± 1.73 | 20.57 ± 1.65 | 20.98 ± 1.28 | 21.88 ± 1.38 |
| 1 h | 19.89 ± 1.33 | 16.92 ± 1.43* | 20.39 ± 1.21^ | 19.47 ± 1.32^ | 14.27 ± 1.34^ |
| 24 h | 18.48 ± 2.39 | 18.74 ± 1.98 | 18.99 ± 1.48 | 19.03 ± 2.48 | 18.13 ± 1.45 |

Note:
Compared with the normal saline group, *$P < 0.05$, **$P < 0.01$.
Compared with the conotoxin positive control group, ^$P < 0.05$, ^^$P < 0.01$.

TABLE 8

Movement distances (m) of mice in the center area in open field tests

| Time | Normal saline | Conotoxin | Polypeptide I | Polypeptide II | Polypeptide III |
|---|---|---|---|---|---|
| 0 | 20.84 ± 1.29 | 21.03 ± 1.73 | 20.57 ±1.65 | 20.98 ±1.28 | 21.88 ±1.18 |
| 1 h | 19.89 ± 1.33 | 16.92 ± 1.43* | 20.39 ± 1.21^ | 19.47 ± 1.32^ | 18.57 ± 1.22^ |
| 24 h | 18.48 ± 2.39 | 18.74 ±1.98 | 18.99 ±1.48 | 19.03 ± 2.48 | 18.13 ±1.38 |

Note:
Compared with the normal saline group, *$P < 0.05$, **$P < 0.01$.
Compared with the conotoxin positive control group, ^$P < 0.05$, ^^$P < 0.01$.

TABLE 9

Movement distances (m) of mice in the peripheral area in open field tests

| Time | Normal saline | Conotoxin | Polypeptide I | Polypeptide II | Polypeptide III |
|---|---|---|---|---|---|
| 0 | 20.84 ± 1.29 | 21.03 ± 1.73 | 20.57 ± 1.65 | 20.98 ± 1.28 | 20.98 ± 1.28 |
| 1 h | 19.89 ± 1.33 | 16.92 ± 1.43* | 20.39 ± 1.21^ | 19.47 ± 1.32^ | 19.47 ± 1.32^ |
| 24 h | 18.48 ± 2.39 | 18.74 ± 1.98 | 18.99 ± 1.48 | 19.03 ± 2.48 | 19.03 ± 2.48 |

Note:
Compared with the normal saline group, *$P < 0.05$, **$P < 0.01$.
Compared with the conotoxin positive control group, ^$P < 0.05$, ^^$P < 0.01$.

Compared with the normal saline group, the polypeptide I group, the polypeptide II group and the polypeptide III group had no significant difference in various indexes in open field experiments, but had significant differences in most of the indexes compared with the conotoxin group, indicating that compared with conotoxin, polypeptide I, polypeptide II and polypeptide III have lower side effects, and can obviously improve adverse conditions such as spontaneous behavior of mice. See tables 3-9 for details. The experimental results have statistical significance.

Example 4

Influence of Analgesic Polypeptides on Anti-Fatigue of Mice in Forced Swimming Tests 1. Materials and Method 1.1 Experimental Animals Forty female Kunming mice were used.

At room temperature of 18-22° C. and in the light for 12 h (6:00-18:00) and in the darkness for 12 h (18:00-6:00), mice had free access to water and food; after 1 week of pre-acclimatization, 20 mice each weighing 18-22 g were selected for the formal experiment (all experiments were conducted at 19:00-24:00).

1.2. Experimental Devices

The experimental devices were all made by our laboratory; and a beaker, a thermostatic water bath, a stop watch, a counter and an ANC Core HD1080P HD camera were provided.

1.3. Method

Before the experiment, 25 mice were divided into negative control group, positive control group, polypeptide I group, polypeptide II group and polypeptide III group according to the random number table. The normal saline group as the negative control group was injected with 0.9% NaCl solution; the conotoxin group with a conotoxin dose of 1 μg/kg was taken as the positive control group; and each polypeptide group had the dosage of 2 nmol/kg. The route of administration was intraperitoneal injection.

The operator put the mice into a round beaker with a diameter of 10 cm and filled with warm water, the water depth was 10 cm and the water temperature was 23-25° C. The duration of movement states of the animals within 5 min was recorded with a camera system. The movement state refers to a state in which an animal actively struggles and its body floats and is twisted. After the observation of all mice, the movement duration of the mice in water was detected again according to the above steps at intervals of 1 h and 24 h, respectively.

2. Experimental Results

TABLE 10

Movement duration (s) of mice in forced swimming tests

| Time | Normal saline | Conotoxin | Polypeptide I | Polypeptide II | Polypeptide III |
|---|---|---|---|---|---|
| 0 | 20.84 ± 1.29 | 21.03 ± 1.73 | 20.57 ± 1.65 | 20.98 ± 1.28 | 21.40 ±1.38 |
| 1 h | 19.89 ± 1.33 | 16.92 ± 1.43* | 20.39 ± 1.21^ | 19.47 ± 1.32^ | 18.57 ± 1.21^ |
| 24 h | 18.48 ± 2.39 | 18.74 ± 1.98 | 18.99 ± 1.48 | 19.03 ± 2.48 | 17.13 ± 1.23 |

Note:
Compared with the normal saline group, *P < 0.05, **P < 0.01.
Compared with the conotoxin positive control group, ˆP < 0.05, ˆˆP < 0.01.

The improvement of exercise tolerance is the most direct manifestation of strengthening the anti-fatigue ability. The swimming duration can reflect the degree of exercise fatigue of animals. Shorter exercise duration indicates greater toxic side effects. The data of forced swimming tests in the polypeptide groups had no significant difference compared with the normal saline group, but most of the data had a significant difference compared with the conotoxin positive control group and a small amount of data had an extremely significant difference. It is showed that compared with the conotoxin, the polypeptides I, II and III have lower toxic side effects. See Table 10 for details. The experimental results have statistical significance.

Example 5

Influence of Analgesic Polypeptides on Anti-Depression of Mice in Tail Suspension Tests
1. Materials and Method
1.1 Experimental Animals
Fifty female Kunming mice were used.
At room temperature of 18-22° C. and in the light for 12 h (6:00-18:00) and in the darkness for 12 h (18:00-6:00), mice had free access to water and food; after 1 week of pre-acclimatization, 20 mice each weighing 18-22 g were selected for the formal experiment (all experiments were conducted at 19:00-24:00).
1.2. Experimental Devices
The experimental devices were all made by the laboratory, including a tail suspension box (20 cm×20 cm×30 cm) which was mounted on side. The peripheral wall and bottom of the box was black, and a stop watch, a counter and an ANC Core HD1080P HD camera were provided.
1.3. Method
Before the experiment, 20 mice were divided into negative control group, positive control group, polypeptide I group, polypeptide II group and polypeptide III group according to the random number table. The normal saline group as the negative control group was injected with 0.9% NaCl solution; the conotoxin group with a conotoxin dose of 1 μg/kg was taken as the positive control group; and each polypeptide group had the dosage of 2 nmol/kg. The route of administration was intraperitoneal injection.

The operator suspended ⅓ of the mouse tail tip in the tail suspension box by using non-cohesive gel so that its head faced the lens about 10 cm from the bottom of the box. The animal's immobility latency within 6 min and the duration of the immobility within 4 min were recorded by the camera system. The immobility refers a state in which an animal gives up active struggle and its body is suspended and not twisted.

2. Experimental Results

TABLE 11

Duration (s) of the immobility of mice in tail suspension tests

| Time | Normal saline | Conotoxin | Polypeptide I | Polypeptide II | Polypeptide III |
|---|---|---|---|---|---|
| 0 | 20.84 ± 1.29 | 21.03 ± 1.73 | 20.57 ± 1.65 | 20.98 ± 1.28 | 19.28 ± 1.02 |
| 1 h | 19.89 ± 1.33 | 16.92 ± 1.43* | 20.39 ± 1.21^ | 19.47 ± 1.32^ | 20.12 ± 1.28 |
| 24 h | 18.48 ± 2.39 | 18.74 ± 1.98 | 18.99 ± 1.48 | 19.03 ± 2.48 | 19.23 ± 1.84 |

Note:
Compared with the normal saline group, *P < 0.05, **P < 0.01.
Compared with the conotoxin positive control group, ˆP < 0.05, ˆˆP < 0.01.

The mouse tried to escape after tail suspension but could not escape, thus giving up the struggle and entering the unique depressed immobility. The animal immobility duration was recorded to reflect the depressive state during the experiment. The shorter tail suspension movement duration indicated the greater toxic side effects. The data of tail suspension test in the polypeptide I group, the polypeptide II group and the polypeptide III group had no significant difference compared with the normal saline group, but most of the data had a significant difference compared with the conotoxin positive control group. It is showed that compared with the conotoxin, the analgesic polypeptides I, II and III have lower toxic side effects. See Table 11 for details. The experimental results have statistical significance.

Example 6

Inhibitory Effect of Analgesic Polypeptides on Pain Inhibition Rates in Formalin-Induced Pain Experiments Persistent pain caused by acute tissue injury was simulated. A diluted formalin solution was injected subcutaneously into the dorsum pedis of one limb of an animal, resulting in behavioral changes of the animal, such as leg bending in silence, limping during exercise, and foot licking. The degree of these behaviors (such as foot licking duration) is proportional to formalin concentration, which is generally considered as a symbol of pain. In addition, other behaviors such as grooming, exploration and sports activities are also affected by formalin injection.

Half male and half female Kunming mice each weighing 20±2 g were used. The indoor temperature was kept at 23-24° C. According to the random number table, mice were grouped into negative control group, positive control group and polypeptide groups respectively, with 10 mice in each group. The group using 0.9% NaCl solution was taken as the negative control group; the conotoxin group with a conotoxin dose of 1 μg/kg was taken as the positive control group; and the analgesic polypeptide groups I, II and III were dosed at 0.2 nmol per mouse. Five minutes after administration, each group of experimental mice were subcutaneously injected with 20 μL of 5% formalin (5% methanol content) solution into the right hind sole of the mice with a 1 mL syringe. The mice were placed in a large glass beaker immediately after injection so that their pain reactions within 1 h were observed, and the duration of licking of the right foot was taken as the behavioral reaction index. A mirror forming an angle of about 30° C. with a platform was placed at the back of the beaker. The cumulative time of licking, biting and shaking of the injected foot every 5 s was recorded with the stop watch from the front and mirror surface. The continuous observation and recording duration was 60 min, phase I (0-10th min) and phase II (10th-60th min), respectively. The analgesic effect of the tested drug after acute administration was investigated by using a formalin-induced inflammatory pain model in mice. The inhibition rates of the positive control group and the conotoxin on phase I and phase II pain reactions were calculated respectively.

$$\text{Inhibition rate \%} = \frac{\text{Pain reaction time of the normal saline group} - \text{Pain reaction time of the tested drug group}}{\text{Pain reaction time of the normal saline group}} \times 100\%$$

Experimental Results:

TABLE 12

Comparison of cumulative foot licking time in Phase I and Phase II of mice in each group

| Group | Phase I | Phase II |
|---|---|---|
| Normal saline group | 68.94 ± 8.32 | 78.0 ± 12.21 |
| Conotoxin group | 50.38 ± 9.38* | 53.64 ± 15.32* |

TABLE 12-continued

Comparison of cumulative foot licking time in Phase I and Phase II of mice in each group

| Group | Phase I | Phase II |
|---|---|---|
| Polypeptide I | 46.44 ± 10.28*^ | 42.10 ± 14.32*^ |
| Polypeptide II | 48.20 ± 11.31*^ | 40.53 ± 14.32 |
| Polypeptide III | 47.19 ± 10.21*^ | 41.23 ± 13.21 |

Note:
Compared with the negative control group, *$P < 0.05$, **$P < 0.01$.
Compared with the positive control group, ^$P < 0.05$, ^^$P < 0.01$.

The data of formalin-induced pain experiments in the groups using the self-designed an algesic polypeptides had a significant difference compared with the normal saline group, and most of the data had a significant difference compared with the conotoxin positive control group. It is showed that polypeptides I, II and III have good analgesic effects. See Table 11 for details. The experimental results have statistical significance.

Example 7

Influence of Analgesic Polypeptides on Neuralgia in a Cancer-Induced Pain (CIP) Model 1. Materials 1.1. Animals A number of male BALB/c mice each weighing 25-30 g were used.

1.2. Experimental Devices and Reagents

Von Fery monofilament; a microsyringe, 5 mg/mL solutions of polypeptides I, II and II I; normal saline.

1.3. Method

BALB/c mice were taken, and the right sciatic nerve was exposed; ascites containing $5\times10^4$ Meth A sarcoma cells were injected into the proximal nerve near the sciatic nerve trochanter far from the tendon branch of the posterior biceps, the wound was closed, and the same volume of normal saline was injected into the left side by performing a sham operation.

1.3.1 Thermosensitive Test

On the 4th, 7th, 10th and 14th days after inoculation, the latency of foot lifting caused by heat radiation stimulation to animals was observed, and the heat radiation intensity was adjusted to cause the latency of foot lifting of normal mice to be (10±2) s.

TABLE 13

Comparison of thermosensitive test results of mice in each group

| Group | Number (n) of animals | Latency of foot lifting before administration | Latency (D) of foot lifting after administration | | | |
|---|---|---|---|---|---|---|
| | | | 4 | 7 | 10 | 14 |
| Control | 10 | 9.85 ± 1.05 | 9.11 ± 1.01 | 8.34 ± 0.87 | 7.92 ± 1.25 | 6.11 ± 0.84 |
| Polypeptide I | 10 | 10.56 ± 0.89 | 10.01 ± 0.23 | 9.26 ± 0.99 | 8.56 ± 0.23 | 7.44 ± 0.85 |
| Polypeptide II | 10 | 10.12 ± 1.64 | 9.87 ± 0.78 | 8.75 ± 0.89 | 8.31 ± 0.92 | 6.56 ± 0.56 |
| Polypeptide III | 10 | 9.77 ± 1.21 | 9.45 ± 1.02 | 8.88 ± 0.86 | 8.26 ± 1.21 | 6.78 ± 1.22 |

1.3.2 Mechanical Sensitivity Test

On the 4th, 7th, 10th and 14th days after inoculation, von Fery monofilament was used to test the mechanical sensitivity of both feet. The threshold of 50% paw withdrawal reaction was determined by a flip test method. The test started at 0.4 g.

1.3.3 Gross Behavior

On the 4th, 7th, 10th and 14th days after inoculation, spontaneous pain and foot drop and the like occurred before the occurrence of thermal sensitivity and mechanical pain sensitivity behaviors, and the cumulative time of lifting the right hind foot within 10 min was calculated.

2. Results

All data was expressed as M±SD and subjected to one-way ANOVA.

2.1 Occurrence of Thermal Sensitization

On the 10th day after inoculation, the latency of foot lifting caused by heat radiation stimulation was significantly shortened by 8 s; on the 14th day after inoculation, the latency was significantly increased by 15 s, and the polypeptide I group was particularly significant.

2.2 Changes in Mechanical Sensitivity

Hypersensitivity to pain and hypersensitivity to heat may occur, and spontaneous pain may also be observed. On the 10th day, von Fery monofilament hypersensitivity to mechanical pain was detected, but on the 14th day, the mice showed hyposensitivity to mechanical pain. There was no difference among the groups.

2.3 Spontaneous Pain Neurologic Syndrome

On the 10th day after inoculation, foot drop was observed in footwork of some mice, and the cumulative duration of lifting the right hind foot slightly increased. On the 14th day, the left foot lifting behavior was obviously observed in the polypeptide I group and the polypeptide II group.

Example 8

Inhibitory Effect of Analgesic Polypeptides on Pain in a Mouse Model for Paclitaxel-Induced Pain 1. Materials 1.1. Animals Male ddY mice (7 weeks old) each weighing 20-25 g were used.

1.2. Experimental Devices and Reagents

A filament mechanical pain threshold detector; fine filaments (equivalent to 0.0688 g of strength); coarse filaments (equivalent to 1.4798 g of strength); paclitaxel; polypeptides I, I I, III; loxoprofen; normal saline.

1.3. Method 1.3.1 Animal Grouping

Mice were fed in an animal room at the temperature of $(22\pm1)°$ C. and the relative humidity of $55\%\pm10\%$ for 1 week and then used for tests. Thirty-six mice were divided into model group (only paclitaxel was administrated), blank control group (no paclitaxel was administrated), loxoprofen group, polypeptide I group, polypeptide II group and polypeptide III group. In the loxoprofen group and the polypeptide groups, the corresponding drugs were given respectively 3 days before the administration of paclitaxel, for a total of 7 days. There were 6 mice in each group.

1.3.2 Experimental Process

Preparation of a model for paclitaxel-induced pain: Mice were intraperitoneally injected with paclitaxel at a dose of 10 mg/kg for modeling.

Behavioral test of pain in mice: The mice were placed on a metal net divided into three compartments and stood for 15 min, and the reaction of mechanical stimulation on the metatarsal part of hind limbs was measured. Allodynia was evaluated with fine filaments first, and then the degree of hyperalgesia was evaluated with coarse filaments. Stimulus responses was performed 5 times for a total of 10 points. Evaluation criteria (0 point: rapid foot lifting action; 2 points: vigorous foot flick or foot licking. The measurement time was before paclitaxel administration and 24, 48, 72 and 96 h after paclitaxel administration).

2. Experimental Results

The measurement data was expressed by M±SD, and T test was adopted for the differences between groups.

TABLE 14

Results of inhibitory effect of polypeptides on pain in a mouse model for paclitaxel-induced pain

| Group | Number (n) of animals | Before administration Allodynia | Before administration Hyperalgesia | 24 h Allodynia | 24 h Hyperalgesia | 48 h Allodynia | 48 h Hyperalgesia | 72 h Allodynia | 72 h Hyperalgesia | 96 h Allodynia | 96 h Hyperalgesia |
|---|---|---|---|---|---|---|---|---|---|---|---|
| Model group | 6 | 0.5 ± 0.2 | 2.3 ± 0.5 | 1.8 ± 0.6 | 5.5 ± 0.6 | 1.5 ± 0.2 | 4.9 ± 0.6 | 0.9 ± 0.5 | 3.5 ± 0.2 | 0.6 ± 0.1 | 2.2 ± 0.3 |
| Blank control group | 6 | 0.6 ± 0.1 | 2.3 ± 0.4 | 0.6 ± 0.1 | 2.2 ± 0.2 | 0.7 ± 0.2 | 2.2 ± 0.3 | 0.6 ± 0.3 | 2.2 ± 0.1 | 0.6 ± 0.2 | 2.3 ± 0.3 |
| Loxoprofen group | 6 | 0.6 ± 0.1 | 2.3 ± 0.5 | 1.4 ± 0.3 | 5.0 ± 0.5 | 0.8 ± 0.3 | 3.6 ± 0.4 | 0.6 ± 0.2 | 2.3 ± 0.3 | 0.6 ± 0.3 | 2.3 ± 0.4 |
| Polypeptide I | 6 | 0.5 ± 0.1 | 2.2 ± 0.6 | 1.4 ± 0.2 | 5.1 ± 0.4 | 0.9 ± 0.3 | 3.6 ± 0.3 | 0.6 ± 0.2 | 2.3 ± 0.2 | 0.6 ± 0.2 | 2.3 ± 0.2 |
| Polypeptide II | 6 | 0.6 ± 0.2 | 2.4 ± 0.2 | 1.5 ± 0.6 | 5.2 ± 0.3 | 1.0 ± 0.4 | 3.7 ± 0.4 | 0.6 ± 0.4 | 2.3 ± 0.4 | 0.6 ± 0.4 | 2.3 ± 0.6 |
| Polypeptide III | 6 | 0.6 ± 0.2 | 2.3 ± 0.8 | 1.5 ± 0.4 | 5.3 ± 0.1 | 1.1 ± 0.1 | 3.7 ± 0.4 | 0.6 ± 0.4 | 2.3 ± 0.2 | 0.6 ± 0.3 | 2.3 ± 0.5 |

2.1 Pain Reaction of Mice after Paclitaxel Administration

When 10 mg/kg paclitaxel was administered intraperitoneally to mice, both allodynia and hyperalgesia peaked at 24 h after paclitaxel administration, then slowly decreased and returned to the pre-administration level after 96 h. In the pain-related scores of 24 h before and after administration, the scores of allodynia were 0.5±0.2 and 1.8±0.6, and those of hyperalgesia were 2.3±0.5 and 5.5±0.6.

2.2 Efficacy of Loxoprofen and Polypeptide Injection

With respect to the influence on allodynia, the pain-related scores of the polypeptide I group, the polypeptide II group and the polypeptide III group were significantly lower than those of the model group ($P<0.05$). Compared with those of the model group, the pain-related scores of the polypeptide groups showed a downward trend with no significant difference. With respect to the influence on hyperalgesia, there was no significant difference between the pain-related scores of the loxoprofen group, the polypeptide I group, the polypeptide II group, the polypeptide III group and the model group.

Example 9

Influence of Analgesic Polypeptides on the Pain Threshold of Trigeminal Nerve
1. Materials
1.1. Animals
SD rats with no gender limitation that each had a weight of 170-200 g were used.

1.2. Experimental Devices and Reagents
A mechanical threshold tester (Stoelting, Wood Dale, USA); a microscope; polypeptides I, II and III; normal saline.
1.3. Method
1.3.1 Animal Model Preparation (All Operations were Completed under Aseptic Conditions).
1.3.2 Positive Criteria for Trigeminal Neuralgia Induction and Model Animals
Adaptive training was performed before the experiment. The trigeminal neuralgia inducing experiment of this model was carried out in a quiet environment at room temperature about 2 weeks after the operation. It can be determined that the model is established when any one or more of the following reactions occur in the rat: (1) Upon stimulation, the rat shows evasive actions such as rapid retreat and turning around, and the rat curls up and draws close to a cage wall to avoid irritants, or hides its head and face under the body to protect its face from being touched by the irritants. (2) The rat scratches its face, showing actions of scratching a facial irritation area continuously at least three times. (3) The rat quickly grabs and bites the irritants and makes aggressive actions.
1.3.3 Experimental Method
Sixty SD rats each weighing 175-200 g with no gender limitation were selected and randomly divided into 6 groups: normal saline control group (6 rats); 50 μg/kg polypeptide I group, polypeptide II group and polypeptide III group each having 6 rats; 100 μg/kg polypeptides I group, polypeptides II group and polypeptides III group each having 6 rats; 300 μg/kg polypeptide I group, polypeptide II group and polypeptide III group each having 6 rats. After allodynia occurred 2 weeks after operation, the animals in each group were injected intraperitoneally with polypeptide injections at 50 μg/kg, 100 μg/kg and 300 μg/kg and normal saline at 0.1 mL/kg respectively, then the pain threshold was measured once every hour for 5 consecutive hours, and pain threshold changes were recorded.

TABLE 15

Results of influence of analgesic polypeptides on the pain threshold of trigeminal nerve

| Group | Number (n) of animals | Dose (μm/kg) | Pain threshold (s) | | | | | |
| --- | --- | --- | --- | --- | --- | --- | --- | --- |
| | | | 0 | 1 | 2 | 3 | 4 | 5 |
| Control group | 6 | 0 | 25.23 ± 0.11 | 23.45 ± 0.21 | 25.65 ± 0.56 | 21.23 ± 0.45 | 22.24 ± 0.45 | 24.23 ± 0.35 |
| Polypeptide I | 6 | 50 | 25.44 ± 0.23 | 26.35 ± 0.65 | 26.89 ± 0.23 | 27.56 ± 0.56 | 26.45 ± 0.78 | 25.89 ± 0.12 |
| Polypeptide I | 6 | 100 | 25.11 ± 0.56 | 27.86 ± 0.95 | 28.12 ± 0.65 | 29.46 ± 0.61 | 26.43 ± 0.62 | 25.68 ± 0.33 |
| Polypeptide I | 6 | 300 | 26.65 ± 0.41 | 30.56 ± 0.11 | 30.53 ± 0.62 | 29.56 ± 0.12 | 28.15 ± 0.32 | 27.15 ± 0.65 |
| Polypeptide II | 6 | 50 | 25.56 ± 0.65 | 25.23 ± 0.44 | 26.62 ± 0.56 | 26.46 ± 0.62 | 27.15 ± 0.56 | 26.62 ± 0.13 |
| Polypeptide II | 6 | 100 | 25.87 ± 0.23 | 26.12 ± 0.62 | 27.16 ± 0.32 | 27.65 ± 0.32 | 26.23 ± 0.62 | 25.13 ± 0.32 |
| Polypeptide II | 6 | 300 | 26.41 ± 0.66 | 30.12 ± 0.56 | 30.61 ± 0.62 | 29.52 ± 0.95 | 28.62 ± 0.61 | 27.92 ± 0.61 |
| Polypeptide III | 6 | 50 | 25.98 ± 0.11 | 26.25 ± 0.46 | 26.69 ± 0.62 | 26.91 ± 0.49 | 27.91 ± 0.26 | 26.91 ± 0.61 |
| Polypeptide III | 6 | 100 | 26.56 ± 0.23 | 27.65 ± 0.61 | 28.16 ± 0.59 | 27.19 ± 0.91 | 28.16 ± 0.61 | 26.16 ± 0.91 |
| Polypeptide III | 6 | 300 | 26.15 ± 0.65 | 31.95 ± 0.56 | 30.21 ± 0.64 | 29.91 ± 0.61 | 28.85 ± 0.41 | 27.92 ± 0.61 |

2. Experimental Results
Experimental data was expressed by M±SD, non-parametric Kruskal-Wallis test, one-way ANOVA and Mann±Whitney u test were used, the area under the aging curve was calculated by a trapezoidal method, and the area under the aging curve between two groups was subjected to T test. P<0.05 means statistical significance.

On the 14th day after operation, the rats had allodynia: the pain threshold on the operative side was reduced to (0.38±0.04) g, the pain threshold on the side opposite to the operative side was (0.43±0.04) g, and the sham-operation group pain threshold was 12.5 g. In this case, after the polypeptides I, II and III injection solutions at 50 μg/kg and 100 μg/kg were injected subcutaneously, the animal reaction thresholds were significantly increased. After injection of the 50 μg/kg polypeptide I group, polypeptide II group and polypeptide III group was performed for 3 h, the highest pain threshold on the operative side was (2.3±0.5) g and the pain threshold on the opposite side was (1.2±0.2) g, and the pain thresholds lasted for 1 h. After injection of the 100 μg/kg polypeptide I group, polypeptide II group and polypeptide III group was performed for 3 h, the highest pain threshold on the operative side was (7.4±0.9) g and the pain threshold on the opposite side was (3.2±1.3) g, and the effect on the operative side lasted for about 8 h. While the pain threshold was not significantly increased in the 300 μg/kg groups injected with polypeptides I, II and III subcutaneously.

SEQUENCE LISTING

SEQ ID NO: 1
Xaa Xaa Cys Ser Thr Pro Pro Xaa Xaa Val Leu Thr Xaa
1               5                   10

SEQ ID NO: 2
Gly Ser Cys Ser Thr Pro Pro Xaa Val Leu Thr Ser
1               5                   10

SEQ ID NO: 3
Gly Ser Cys Ser Thr Pro Pro Ser Ala Val Leu Thr Cys
1               5                   10

SEQ ID NO: 4
Leu Cys Ser Thr Pro Pro Asp Asp Val Leu Thr Cys
1               5                   10

SEQ ID NO: 5
Gly Ile Cys Cys Val Asp Asp Thr Cys Thr Thr His Ser Gly Cys Leu
1               5                   10                  15

SEQ ID NO: 6
Gly Cys Cys Ser Thr Pro Pro Cys Ala Val Leu Thr Cys
1               5                   10

SEQUENCE LISTING

<160> NUMBER OF SEQ ID NOS: 6

<210> SEQ ID NO 1
<211> LENGTH: 13
<212> TYPE: PRT
<213> ORGANISM: Artificial Sequence
<220> FEATURE:
<223> OTHER INFORMATION: Synthetic sequence
<220> FEATURE:
<221> NAME/KEY: VARIANT
<222> LOCATION: (1)..(13)
<223> OTHER INFORMATION: From the N-terminus, the 1st X is Gly or
      deleted, the 2nd X is one of Ser or Lys; the 3rd X is one of d-Cys
      or Ser or Asp, the 4th X is Ala or deleted; and the 5th X is Cys
      or Ser

<400> SEQUENCE: 1

Xaa Xaa Cys Ser Thr Pro Pro Xaa Xaa Val Leu Thr Xaa
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (8)..(8)
<223> OTHER INFORMATION: X is d-Cys

<400> SEQUENCE: 2

Gly Ser Cys Ser Thr Pro Pro Xaa Val Leu Thr Ser
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Synthetic sequence

<400> SEQUENCE: 3

```
Gly Ser Cys Ser Thr Pro Pro Ser Ala Val Leu Thr Cys
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Synthetic sequence

<400> SEQUENCE: 4

Leu Cys Ser Thr Pro Pro Asp Asp Val Leu Thr Cys
1               5                   10

<210> SEQ ID NO 5
<211> LENGTH: 16
<212> TYPE: PRT
<213> ORGANISM: Artificial Sequence
<220> FEATURE:
<223> OTHER INFORMATION: Synthetic sequence

<400> SEQUENCE: 5

Gly Ile Cys Cys Val Asp Asp Thr Cys Thr Thr His Ser Gly Cys Leu
1               5                   10                  15

<210> SEQ ID NO 6
<211> LENGTH: 13
<212> TYPE: PRT
<213> ORGANISM: artificial sequence
<220> FEATURE:
<223> OTHER INFORMATION: Synthetic sequence

<400> SEQUENCE: 6

Gly Cys Cys Ser Thr Pro Pro Cys Ala Val Leu Thr Cys
1               5                   10
```

What is claimed is:

1. A polypeptide with analgesic activity, wherein the amino acid sequence of the polypeptide is $X_a$-$X_b$-Cys-Ser-Thr-Pro-Pro-$X_c$-$X_d$-Val-Leu-Tyr-$X_e$ (SEQ ID NO: 1) or a pharmaceutically acceptable salt thereof and wherein $X_a$ is Gly or absent, $X_b$ is Ser or Lys, $X_c$ is D-Cys, Ser, or Asp, $X_d$ is Ala or absent, and $X_e$ is Cys or Ser.

2. The polypeptide with analgesic activity according to claim 1, wherein the amino acid sequence of the polypeptide is:

polypeptide I:
(SEQ ID NO: 2)
Gly-Ser-Cys-Ser-Thr-Pro-Pro-d{Cys}-Val-Leu-Tyr-Ser;

polypeptide II:
(SEQ ID NO: 3)
Gly-Ser-Cys-Ser-Thr-Pro-Pro-Ser-Ala-Val-Leu-Tyr-Cys;
or polypeptide III:
(SEQ ID NO: 4)
Lys-Cys-Ser-Thr-Pro-Pro-Asp-Ala-Val-Leu-Tyr-Cys.

3. The polypeptide with analgesic activity according to claim 2, wherein one pair of disulfide bonds are formed between two cysteines in each of the polypeptide sequence.

4. A product for preventing and/or treating pain, wherein the active ingredient is the polypeptide of claim 2.

5. The product for preventing and/or treating pain according to claim 4, wherein the pain comprises physicochemical irritating pain and pathological or neuropathic pain.

* * * * *